(12) United States Patent
Wood

(10) Patent No.: US 8,889,240 B2
(45) Date of Patent: Nov. 18, 2014

(54) STRETCH RELEASE ARTICLE

(71) Applicant: 3M Innovative Properties Company, St. Paul, MN (US)

(72) Inventor: Leigh E. Wood, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/730,125

(22) Filed: Dec. 28, 2012

(65) Prior Publication Data

US 2014/0186566 A1 Jul. 3, 2014

(51) Int. Cl.
| | | |
|---|---|---|
| *B32B 9/00* | (2006.01) | |
| *B32B 33/00* | (2006.01) | |
| *B32B 7/12* | (2006.01) | |
| *C09J 7/02* | (2006.01) | |
| *A61F 13/15* | (2006.01) | |

(52) U.S. Cl.
CPC . *C09J 7/02* (2013.01); *A61F 13/15* (2013.01); *C09J 7/0246* (2013.01); *C09J 2201/128* (2013.01); *C09J 2201/28* (2013.01); *C09J 2201/606* (2013.01); *C09J 2201/618* (2013.01); *C09J 2409/00* (2013.01); *C09J 2423/106* (2013.01); *C09J 2425/00* (2013.01); *C09J 2453/00* (2013.01)
USPC .......... 428/40.1; 428/42.1; 428/343; 428/354

(58) Field of Classification Search
CPC ........... A61F 13/15; C09J 7/02; C09J 7/0256; C09J 2201/128; C09J 2201/28; C09J 2201/606; C09J 2201/618; C09J 2409/00; C09J 2423/106; C09J 2425/00; C09J 2453/00
USPC ........................ 428/40.1, 41.9, 42.1, 343, 354
See application file for complete search history.

(56) References Cited

U.S. PATENT DOCUMENTS

| 3,562,356 | A | | 2/1971 | Nyberg |
| 3,643,662 | A | | 2/1972 | McGuire |
| 3,700,633 | A | | 10/1972 | Wald |
| 3,885,559 | A | | 5/1975 | Economou |
| 4,024,312 | A | * | 5/1977 | Korpman ...................... 428/343 |
| 4,116,917 | A | | 9/1978 | Eckert |
| 4,156,673 | A | | 5/1979 | Eckert |
| 5,376,430 | A | | 12/1994 | Swenson |

(Continued)

FOREIGN PATENT DOCUMENTS

| EP | 2579555 | 4/2013 |
| GB | 2339710 | 2/2000 |
| WO | WO 01/14488 | 3/2001 |

OTHER PUBLICATIONS

International Search Report PCT/US2013/074517; Mar. 17, 2017; 4 pages.

*Primary Examiner* — Patricia L Nordmeyer
(74) *Attorney, Agent, or Firm* — Philip P. Soo

(57) ABSTRACT

Provided are adhesive articles and assemblies that include a flat and at least partially elastic backing along with a patterned adhesive coating on each side of the backing. When viewed from directions perpendicular to the backing, the adhesive on one side of the backing does not substantially overlap the adhesive on the opposing side of the backing. As a result, it is possible to use a stretch removable adhesive article that uses, for example, an aggressive adhesive to provide a reliable bond but still remove cleanly and easily from delicate substrates that would otherwise be damaged or destroyed if bonded with conventional adhesive constructions.

26 Claims, 7 Drawing Sheets

(56) References Cited

U.S. PATENT DOCUMENTS

| | | | |
|---|---|---|---|
| 5,516,581 A | 5/1996 | Kreckel | |
| 5,589,246 A * | 12/1996 | Calhoun et al. | 428/120 |
| 5,622,761 A | 4/1997 | Cole | |
| 5,725,923 A | 3/1998 | Lühmann | |
| 6,200,298 B1 | 3/2001 | Osborn, III | |
| 6,410,135 B1 | 6/2002 | Hamerski | |
| 6,436,529 B1 | 8/2002 | Deeb | |
| 6,541,089 B1 | 4/2003 | Hamerski | |
| 6,641,910 B1 | 11/2003 | Bries | |
| 6,866,928 B2 | 3/2005 | Narum | |
| 7,078,582 B2 | 7/2006 | Stebbings | |
| 7,101,615 B2 | 9/2006 | Lühmann | |
| 2002/0090496 A1 | 7/2002 | Kim | |
| 2004/0202841 A1 | 10/2004 | Jour | |
| 2011/0202029 A1 | 8/2011 | Toro | |

* cited by examiner

STRETCH RELEASE ARTICLE

FIELD OF THE INVENTION

Provided are dual-sided adhesive articles for adhering opposing substrates to each other. More particularly, the dual-sided adhesive articles are stretch removable from at least one of the substrates without damage to that substrate.

BACKGROUND

Stretch removable adhesive articles provide temporary bonding solutions in a wide variety of commercial and industrial applications. These adhesive articles can be easily removed from a bonded substrate by stretching the article lengthwise in a direction substantially parallel to the plane of the substrate. Because the adhesion substantially degrades as the adhesive is elongated, the stretching action enables the adhesive to be conveniently detached without damaging the underlying substrate. These articles are commonly used to bond two different substrates to each other, thus allowing two adhesively bonded materials to be separated from each other without damage to either substrate.

Commercial stretch removable adhesive articles include COMMAND brand adhesive tapes sold by 3M Company, St. Paul, Minn. and POWER-STRIPS brand self-adhesive tapes sold by Beiersdorf AG, Hamburg, Germany. These products can be optionally provided with long discrete strips of a pressure sensitive adhesive with a pull tab at one end to facilitate stretching of the strips during removal. Optionally, the adhesive areas can be protected using a release liner prior to use. In some cases, it is advantageous for the adhesive to undergo inelastic deformation as it stretches to avoid sudden recoil, or "snap," when the adhesive fully detaches. An ancillary benefit of inelastic deformation during stretching is that such products do not return to their original shape, thereby indicating if the product has been previously used or tampered with.

Adhesive tapes and films that are stretch removable can be especially useful in bonding to soft and/or delicate surfaces. For example, such articles have been used for temporary attachment of paper articles, such as for holding posters, signs, or other large format graphics, or even bonding to skin in medical tape, wound or surgical dressing, athletic tape, surgical drape, and medical device applications. Finally, these articles can also be used to facilitate attachment of other articles to clothing, as commonly used in adult incontinence pads or feminine hygiene products such as absorbent sanitary napkins, which are adhered to undergarments. These types of applications pose unique challenges not only because of the flexibility of the substrate but also the need to reconcile the demand for high levels of adhesion with the need to avoid inadvertent damage to the substrate during removal.

SUMMARY

Engineering a removable adhesive can present unique challenges with respect to user experience. In some applications, users find that a peel action is a more intuitive way to remove an article adhesively bonded to a substrate. Yet, detachment from the substrate does not effectively occur with conventional stretch removable adhesives unless the adhesive is stretched lengthwise in a direction substantially parallel to the plane of the substrate surface. As a result, undue force may be required to remove the adhesive, or even worse, adhesive residue may be left on the surface of the substrate after removal. While this problem may be addressed by using a less aggressive adhesive, such a solution is often inadequate when bonding to garments.

Products intended for adhesion to garments can face particular challenges resulting from certain types of garment movements during use. These movements may include longitudinal and transverse extension as well as twisting movements, which may impose stresses on the adhesive. A common failure mode for feminine hygiene products is the partial detachment or shifting of the adhesive induced by twisting and shearing type movements of the garment relative to feminine hygiene products. These movements, which often occur as a result of walking, can cause the hygiene product to slowly migrate from its intended position. If the stresses are sufficiently large, these movements can even cause the adhesive to completely detach from the undergarment. Also problematic is "bunching" of the garment, which can cause a partially detached adhesive to buckle and become permanently adhered to itself.

It was discovered that these problems can be overcome by using an adhesive article that includes a substantially elastic backing and a patterned adhesive coating on each side. When viewed in cross-section, the adhesive on one side of the backing substantially does not overlap the adhesive on the opposing side of the backing. As a result, it is possible to enable a stretch removable adhesive article that uses an aggressive adhesive to provide a reliable bond and still removes cleanly and easily from delicate substrates, such as paper or undergarments, that would otherwise be damaged or destroyed if bonded using conventional adhesive articles. As a further benefit, these adhesive articles display superior stretch characteristics which help avoid detachment of the adhesive from the garment even when the garment is subjected to extreme twisting and shear type movements.

In one aspect, a dual-sided adhesive article is provided. The adhesive article comprises: a flat and substantially elastic backing having first and second major surfaces; a first adhesive extending across the first major surface according to a two-dimensional first pattern; and a second adhesive extending across the second major surface according to a two-dimensional second pattern, wherein the first and second patterns do not substantially overlap with each other when the first and second patterns are projected onto a reference plane parallel to the backing.

In another aspect, an adhesive assembly is provided comprising: a substrate; and a dual-sided adhesive article contacting the substrate, the dual-sided article comprising: a flat and substantially elastic backing having first and second major surfaces; a first adhesive extending across the first major surface and adhering the backing to the substrate along a two-dimensional first pattern; a second adhesive extending across the second major surface according to a two-dimensional second pattern, wherein the first and second patterns do not substantially overlap with each other when the first and second patterns are projected onto a reference plane parallel to the backing.

In still another aspect, a method of making a feminine hygiene pad is provided, comprising: providing a flat and substantially elastic backing having first and second major surfaces; adhesively coupling a release liner to the first major surface using a first adhesive coated according to a first two-dimensional pattern; and adhesively coupling an absorbent article to the second major surface using a second adhesive coated according to a second two-dimensional adhesive pattern, wherein the first and second patterns do not substantially overlap with each other when each is projected onto a common reference plane coplanar with the backing.

DETAILED DESCRIPTION

Described in further detail herein are articles and assemblies that use a stretch removable adhesive along with associated methods of making and using the same. Stretch removable articles and assemblies, while broadly examined here, can be customized for any of a number of applications including medical, industrial, and consumer products. In particular, these constructions can be specialized for bonding articles to various substrates, including both rigid substrates (e.g. walls) and flexible substrates (e.g. clothing).

These configurations can be rendered in both simple and compound constructions; for example, the provided articles and assemblies can be implemented as a dual-sided tape, a substrate pre-coated with such a tape, or two or more substrates coupled to each other by such a tape. Each substrate may be either permanently or temporarily coupled to the tape. The substrates themselves may be functional, ornamental, or both. While particular embodiments are described here by way of illustration and example, these should not be deemed to unduly restrict the scope of the claimed invention.

Figure 1:
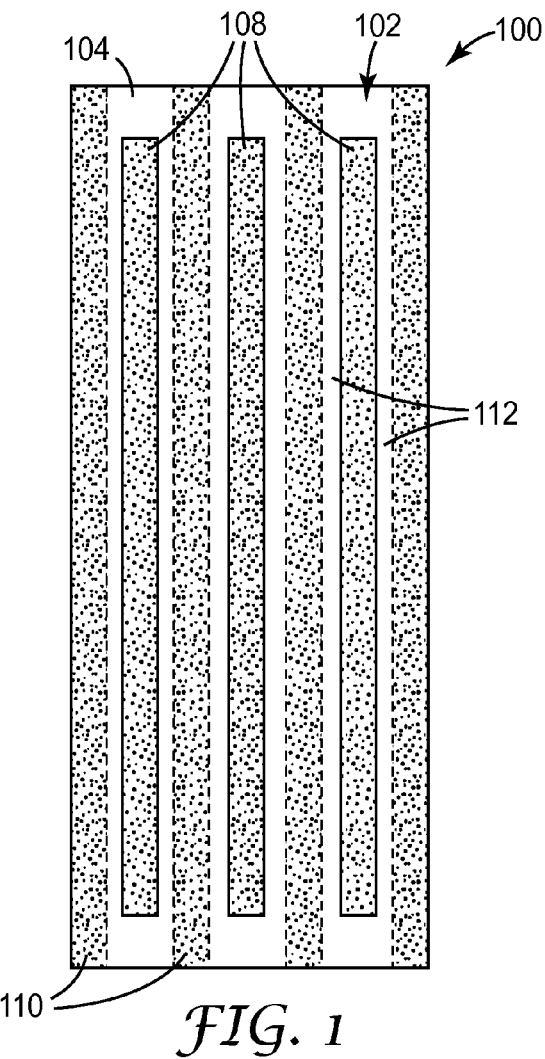
FIG. 1 shows a plan view of a dual-sided adhesive article according to one embodiment, looking toward its top surface.
Figure 2:
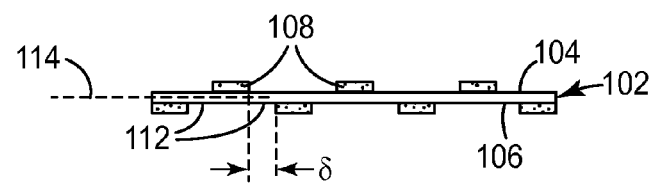
FIG. 2 shows an elevational side view of the article of FIG. 1, rotated 90 degrees and looking toward its side surface.

An adhesive article according to one exemplary embodiment is shown in FIGS. 1 and 2, and designated by the numeral 100. In plan view, the article 100 is generally rectilinear as shown, but could also have rounded edge contours if desired. The article 100 is generally planar when relaxed, although the article 100 could optionally be converted into a roll for a compact storage and dispensing. The article 100 includes a generally planar backing 102. As shown in FIG. 2, the backing 102 has two major surfaces, a top surface 104 and a bottom surface 106.

Suitable materials for the backing 102 include polymeric sheet materials that display high elasticity, high strength, and high tensile strength to function properly during stretch removal of the article 100. Exemplary backings 102 preferably have an elastic recovery of at least about 70 percent, at least about 80 percent, or at least about 90 percent based on an elongation of 100 percent. Such backings 102 could also, in some embodiments, have an elastic recovery of at most about 95 percent, at most about 85 percent, or at most about 70 percent based on an elongation of 100 percent.

Percent elongation=$(L_s-L_o)/L_o \times 100$ where $L_o$ is original length $L_s$ is stretched length. Also sometimes the duration of hold at stretch condition is mentioned as in stretched to 100 percent and immediately relaxed. The equation for elastic recovery is then:

Percent recovery=$(L_s-L_r/L_o) \times 100$, where $L_o$ and $L_s$ are as defined above and $L_r$ is length after relaxation from stretch (usually a time period is given for the relaxation such as 5 minutes).

It is also preferred that the backing 102 have a sufficient range of elongation that enables removal of the adhesive from the underlying substrate on demand. In some embodiments, the backing 102 has a lengthwise elongation at break of at least about 50 percent, at least about 150 percent, or at least about 350 percent. In some embodiments, the lengthwise elongation at break is at most about 1,200 percent, at most about 900 percent, or at most about 700 percent.

In preferred embodiments, the tensile strength at break of the backing 102 is sufficiently high so that the backing 102 will not rupture prior to or during removal of the adhesive article 100 from the surface to which it has been adhered. The tensile strength at break of the backing 102 is preferably at least about 4.3 ksi, more preferably at least about 5.3 ksi, and most preferably at least about 6.3 ksi.

Examples of materials particularly suitable for the backing 102 of the article 100 include any material capable of being formed into a thin film layer and exhibiting elastomeric properties at ambient conditions. Elastomeric means that the material will substantially resume its original shape after being stretched. The elastomer can be both pure elastomers and blends with an elastomeric phase or content that will still exhibit substantial elastomeric properties at room temperature.

Suitable elastomers include such elastomeric polymers known to those skilled in the art as AB and ABA block copolymers. Star or radial block copolymers may also be suitable in the present invention. Elastomeric block copolymers are typically thermoplastic rubbers that have a rubbery midblock with at least two high glass transition temperature endblocks. Block copolymers are described, for example, in U.S. Pat. No. 3,562,356 (Nyberg et al.); U.S. Pat. No. 3,700,633 (Wald et al.); U.S. Pat. No. 4,116,917 (Eckert); and U.S. Pat. No. 4,156,673 (Eckert).

There are at least two basic classes of these polymers. In one class, the midblock is an unsaturated rubber. Examples of two types of polymers in this class are known to those skilled in the art as SBS and SIS block copolymers. In the other class, the midblock is a saturated olefin rubber. Examples of two types of polymers in this class are known to those skilled in the art as SEBS and SEPS block copolymers. SIS, SBS, SEBS, and SEPS block copolymers are useful in the present invention, with SIS block copolymers being preferred because of the elastomeric properties exhibited by these polymers.

Other useful elastomeric compositions may include elastomeric polyurethanes, ethylene copolymers such as ethylene vinyl acetates, ethylene/propylene copolymer elastomers or ethylene/propylene/diene terpolymer elastomers. Blends of these elastomers with each other or with modifying non-elastomers may also be useful. For example, up to 50 weight percent, but preferably less than 30 weight percent, of polymers may be added such as poly(alpha-methyl)styrene, polyesters, epoxies, polyolefins, e.g., polyethylene or certain ethylene/vinyl acetates, preferably those of higher molecular weight, or coumarone-indene resin.

The backing 102 preferably has a composition that is compatible with the adhesive or adhesives used in the construction. For example, an adhesive disposed thereon should form a strong bond with the surface of the backing 102, thereby avoiding undesirable adhesive transfer during stretch removal of the article 100 from a substrate. Another consideration is the problem of cross-contamination which could occur when the backing 102 is placed in contact with certain adhesives. In some preferred constructions, the backing 102 includes a sandwich construction where a protective polyolefin skin layer is disposed on each major surface of an elastomeric core layer. Protective layers can prevent tackifiers in an adhesive from migrating into the elastic film and causing the adhesive to lose tack over time.

Other aspects of elastomeric materials suitable for the backing 102 are described in U.S. Pat. No. 5,376,430 (Swenson et al.) and U.S. Pat. No. 6,436,529 (Deeb et al.).

The backing 102 can be made by any method of film forming presently known in the art, such as extrusion, co-extrusion, solvent casting, foaming, and the like. Use of a non-woven technology to form the backing 102 is also possible. The backing 102 can have any thickness so long as it possesses sufficient integrity to be easily processed and handled. Preferably, the backing 102 has a thickness ranging from about 10 micrometers to 250 micrometers. In the preferred range, thinner backings can sometimes provide easier removal than thicker ones.

Referring again to FIGS. 1 and 2, a first series of parallel adhesive strips 108 contact and longitudinally extend across the top surface 104 of the backing 102. Additionally, a second series of adhesive strips 110 contact and longitudinally extend along the bottom surface 106 of the backing 102. In FIG. 1, the second series of adhesive strips 110 can be observed through the translucent backing 102, although this need not be the case in general. This particular embodiment shows an asymmetric adhesive layer arrangement, with three strips 108 disposed on the top surface 104 and four strips 110 disposed on the bottom surface 106. More or fewer strips may be used on either of the top or bottom surfaces 104, 106.

The first strips 108 do not extend to the edges of the article 100, while the second strips 110 extend to the edges of the article 100. In FIG. 1, this is manifested by the terminal ends of the former being spaced apart from the terminal edge of the underlying backing 102 and the terminal ends of the latter being flush with the terminal edge of the backing 102. This feature can provide particular advantages in initiating proper adhesive removal from a substrate, as will be discussed later.

As shown, each series of adhesive strips 108, 110 extends across its respective top or bottom surface 104, 106 according to a pre-defined two-dimensional pattern. The term "pattern," as used herein, broadly refers to a plurality of replicated features, or "repeat units." In preferred embodiments, each two-dimensional pattern has a defined repeat unit that is replicated across the backing 102. The repeat units are further characterized by a repeat dimension, corresponding to the shortest distance a repeat unit is moved to superimpose on an adjacent repeat unit of the pattern. More than one repeat dimension may exist—for example, two different repeat dimensions may be oriented along respective x and y axes of the two-dimensional pattern.

In FIGS. 1 and 2, the patterns represent discrete and parallel elongated strips having a fixed width, length, and repeat dimension. The first and second patterns correspond to respective first and second series of strips 108, 110, and do not overlap with each other when the respective patterns are projected onto a common reference plane 114 coplanar with the backing 102. As a result, areas of the backing 102 that are coated on one surface 104, 106 of the backing are uncoated on the opposite surface 104, 106, and vice versa. Stated inversely, this configuration avoids having regions of the backing 102 where adhesive is coated on both sides.

As shown in FIGS. 1 and 2, the first and second patterns as projected onto the reference plane 114 are spaced apart from each other by a transverse gap 112. As shown, the gap 112 is characterized by a gap width $\delta$, and extends in a direction perpendicular to the strips 108, 110 along the plane of the backing 102. Areas of the backing 102 within the gap 112 are bare; that is, these areas are not coated on either the top or bottom surfaces 104, 106 of the backing 102.

While the gap 112 here essentially represents the lateral space between the nearest edges of adjacent strips 108, 110, the gap 112 more broadly represents the area of separation between respective projections of the adhesive layer patterns disposed on opposite sides of the backing 102. In some embodiments, the gap width $\delta$ is not constant but variable. For example, if the adhesive strips are not parallel, the gap width $\delta$ would have a range of values. In some embodiments, the adhesive layer patterns overlap, resulting in a "negative" gap in these locations. When the gap width $\delta$ is not constant, the gap 112 could be characterized by an average gap width $\delta$ based on an integrated average of differential gap widths along the perimeter of each pattern feature.

While the gap 112 can significantly affect the release characteristics of the article 100, it is not essential. In some embodiments, for example, there is neither a positive nor negative gap between the first and second patterns when projected onto the reference plane 114. In this "zero gap" configuration, the projection of the second pattern on the reference plane 114 is in perfect registration with the inverse of the projection of the first pattern. Even where the gap 112 is small, these two patterns could be considered substantially in registration with each other.

By facilitating elongation of the backing 102, the gap 112 provides a useful engineering variable to tailor stretch removal of the adhesive article 100 from a given substrate. Notably, when the adhesive article 100 adhesively bonds two substrates to each other, areas of the backing 102 within the gap 112 are not "pinned" to either substrate. As a result, the same amount of force causes the backing 102 to stretch to a greater extent, further resulting in a greater ease of opening in a peel mode. Another benefit of the gap 112 is the reduction in unit costs to manufacture the adhesive article 100, because less adhesive is required to coat the backing 102 as the gap width $\delta$ increases and coating area decreases.

In some embodiments, the gap 112 has a gap width $\delta$ (or average gap width $\delta$) of at least about 10 percent, at least about 25 percent, at least about 50 percent, at least about 100 percent, or at least about 200 percent of the repeat dimension for either the first or second pattern. In some embodiments, the gap width $\delta$ (or average gap width $\delta$) is at most about 500 percent, at most about 400 percent, at most about 300 percent, at most about 250 percent, or at most about 200 percent of the repeat dimension for either the first or second pattern.

The gap 112 is inversely related to the cumulative degree of coverage of the first and second patterns with respect to the backing 102. In some embodiments, the adhesive coating areas defined by the first and second patterns collectively extend across an area representing at least about 10 percent, at least about 15 percent, at least about 25 percent, at least about 50 percent, or at least about 75 percent of the overall surface area of the backing 102 (the combined surface area of the top and bottom surfaces 104, 106). In some embodiments, the adhesive coating areas defined by the first and second patterns collectively extend across an area representing at most about 95 percent, at most about 90 percent, at most about 60 percent, at most about 30 percent, or at most about 10 percent of the overall surface area of the backing 102.

The arrangement of the coated patterns can help achieve a particular mode of removal from a given substrate. For example, the asymmetric coating configuration in FIGS. 1 and 2 (with three adhesive strips 108 opposing four adhesive strips 110) tends to induce preferential removal from the substrate bonded to the fewer and shorter adhesive strips 108. A similar advantage is obtained by virtue of the adhesive strips 110 having terminal edges flush with that of the backing 102 and the adhesive strips 108 having terminal edges spaced apart from that of the backing 102. The four adhesive strips 110 collectively anchor the adjacent substrate to the backing 102 as the article 100 is initially peeled, concentrating the peel forces against the seam between the adhesive strips 108 and the opposing substrate to initiate removal along that preferred interface.

In some embodiments, the first and second adhesives extend across similar overall coating areas with respect to each other on respective top and bottom surfaces 104, 106. In some embodiments, the first adhesive is the majority coating and extends across at least about 30 percent, at least about 40 percent, at least about 50 percent, at least about 60 percent, or at least about 75 percent of the top surface 104. In some embodiments, the first adhesive extends across at most about 90 percent, at most about 85 percent, at most about 80 percent, at most about 75 percent, or at most about 70 percent of the top surface 104.

Alternatively, the coating area of the first adhesive can be quantified as a percentage of the coating area of the second adhesive. In some embodiments, the second adhesive is a minority coating and extends across a coating area of at most about 90 percent, at most about 85 percent, at most about 80 percent, at most about 75 percent, or at most about 70 percent of the overall coating area of the first adhesive. In some embodiments, the second adhesive extends across a coating area of at least about 30 percent, at least about 40 percent, at least about 50 percent, at least about 60 percent, or at least about 70 percent of the overall coating area of the first adhesive.

The coating weight of the first or second adhesive, which relates to adhesive layer thickness, can be adjusted as needed based on the materials and application. In some embodiments, the first or second adhesive has a coating weight of at least about 5 gsm, at least about 10 gsm, at least about 20 gsm, at least about 35 gsm, or at least about 50 gsm of the coated area of the backing 102. In some embodiments, the first or second adhesive has a coating weight of at most about 100 gsm, at most about 90 gsm, at most about 75 gsm, at most about 60 gsm, or at most about 50 gsm of the coated area of the backing 102.

In some cases, it is desirable for the first and second adhesive to have sufficient elasticity so not to interfere with the recovery of the backing 102 when it is stretched during peel. This can be especially beneficial, for example, in a consumer application where the adhesive article 100 may require repositioning on a garment after being improperly positioned on the first attempt.

The precise nature of the first and second patterns need not be limiting. While the first and second patterns define elongated stripes in FIGS. 1 and 2, many other patterns are possible. For example, a suitable pattern could include a replicated array of triangles, rectangles, circles, or any number of other two-dimensional shapes. Further, a pattern can include continuous features, discontinuous features, or combination of both. Randomized patterns having replicated features arranged in an irregular two-dimensional arrangement, such as a randomized dot pattern, can also be used. Replicated features need not be identical to each other; for example, a pattern of replicated circles may include circles having different diameters.

The first and second adhesive strips 108, 110 themselves are preferably composed of a pressure-sensitive adhesive ("PSA"). In some embodiments, the same adhesive is used for both the first and second adhesive strips 108, 110. Alternatively, the first and second adhesive strips 108, 110 could use different adhesives. This could be advantageous where it is desirable to optimize at least one of the adhesives for specific performance characteristics or end uses. Choice of adhesives could be used, for example, to facilitate preferential removal with respect to one substrate over the other.

The particular adhesion properties can be at least partially dependent on the mode of measurement. Preferred adhesion properties generally range from about 13 N/dm to about 200 N/dm, preferably from about 25 N/dm to about 100 N/dm, at a peel angle of 180 degrees, measured according to PSTC-1 and PSTC-3 and ASTM D 903-83 at a peel rate of 12.7 cm/min. A backing 102 having a higher tensile strength may be used for adhesives with high peel adhesion.

PSAs suitable for this invention include tackified rubber adhesives, such as natural rubber, olefins, silicones, polyisoprene, polybutadiene, polyurethanes, styrene-isoprene-styrene and styrene-butadiene-styrene block copolymers, and other elastomers, and tackified or untackified acrylic adhesives such as copolymers of isooctylacrylate and acrylic acid, which can be polymerized by radiation, solution, suspension, or emulsion techniques. Crosslinked adhesives are preferred, especially those PSAs crosslinked to provide high shear strengths. Particularly preferred adhesives include those crosslinked by radiation with or without a chemical crosslinking agent. Adhesives that have high shear strength provide low debonding force and can easily be removed when stretched.

For applications such as feminine hygiene pads, it may be preferred to use tackified synthetic rubber type adhesives rather than radiation or otherwise cross-linked adhesives. Advantageously, the former adhesives can be melted in the bulk and subsequently applied to the backing. These materials include, for example, SIS block copolymer adhesives. Although the styrene ("S") domains in SIS-type adhesives are viewed as crosslinks they are not covalent in nature and can be melted.

The adhesive article 100 can be produced by any known method for preparing pressure-sensitive adhesive articles. For example, one or both of the adhesive strips 108, 110 can either be directly coated onto the backing 102, or they can be formed as a separate layer and then later laminated to the backing 102. As another example, one or both of the adhesive strips 108 could be coated onto a respective substrate and then adhesively coupled to the backing 102. In one exemplary embodiment, the backing 102 is part of a continuously conveyed web and pattern coated using intermittent adhesive applicators, the applicators being precisely positioned on opposite sides of the backing 102 and operating in registration with each other to produce the adhesive article 100. The same process could be used to laminate subsequently a suitable substrate to one or both sides of the article 100.

To improve adhesion of the adhesive strips 108, 110 to the backing 102, the backing 102 can optionally be pretreated prior to the coating or laminating step by corona discharge, plasma discharge, flame treatment, electron beam irradiation, ultraviolet radiation, acid etching, and/or chemical priming. Such pretreatments can be carried out with or without reactive chemical adhesion promoters such as hydroxyethyl acrylate or hydroxyethyl methacrylate, or other reactive species of low molecular weight.

Alternative Geometries

Figure 3:
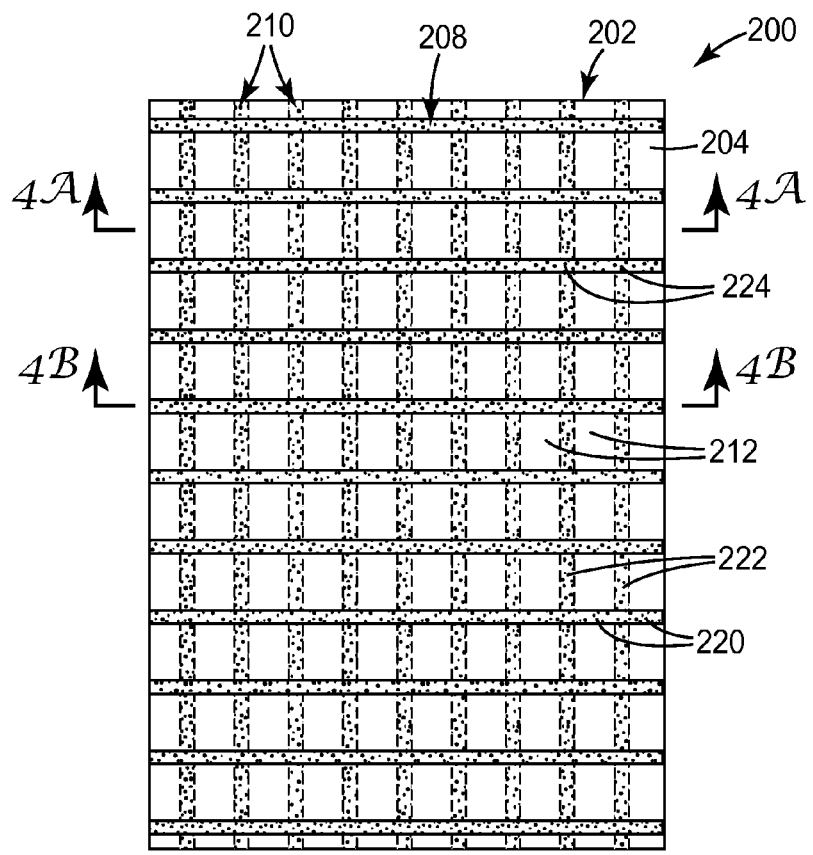
FIG. 3 shows a plan view of a dual-sided adhesive article according to another embodiment, looking toward its top surface.
Figure 4A:
FIGS. 4A-B show two cross-sectional side views of the article of FIG. 3, as defined by consecutive section planes indicated in FIG. 3.
Figure 4B:
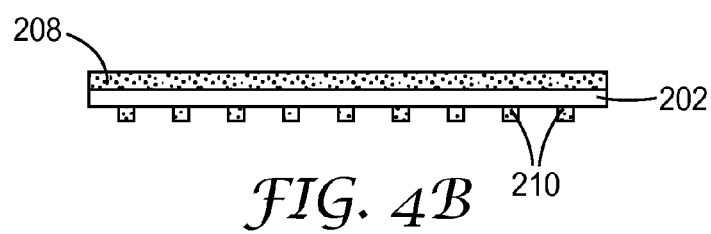
Figure 5:
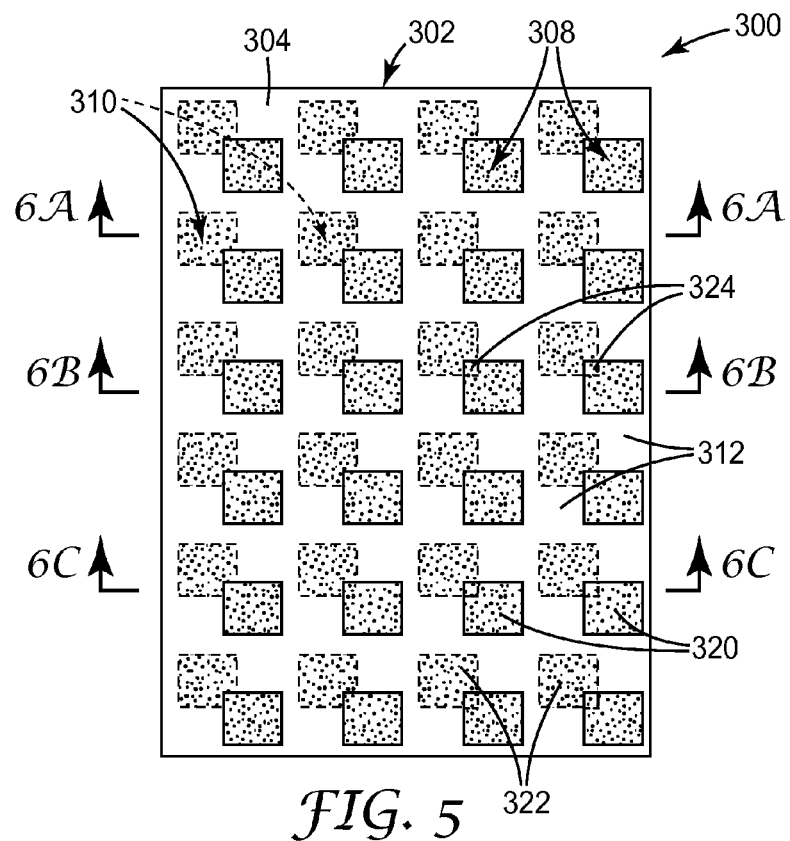
FIG. 5 shows a plan view of a dual-sided adhesive article according to yet another embodiment, looking toward its top surface.
Figure 6A:
FIGS. 6A-C show three cross-sectional side views of the article of FIG. 5, as defined by consecutive section planes indicated in FIG. 5.
Figure 6B:
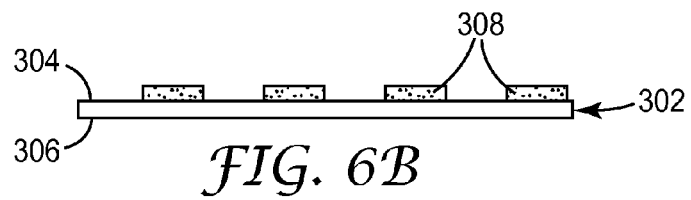
Figure 6C:
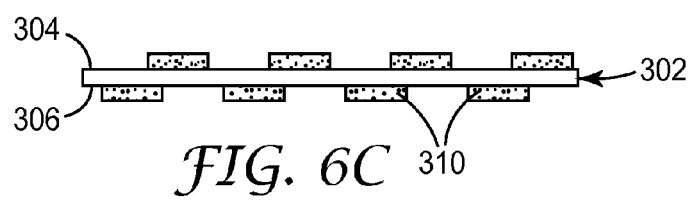

A small degree of overlap between the projected first and second patterns representing adhesive layers on opposite sides of the backing can be tolerated. This is demonstrated by an adhesive article 200 according to another exemplary embodiment illustrated in plan view and cross-section in respective FIGS. 3 and 4A-B. Like article 100, the article 200 includes a generally flat, planar, and continuous elastic backing 202, with two sets of elongated adhesive strips 208, 210 contacting and extending across respective first and second major surfaces 204, 206 of the backing 202. As shown in FIG. 3, strips 208 are parallel with each other; likewise, strips 210 are parallel with each other.

Unlike in the article 100, however, the opposing sets of adhesive strips 208, 210 do not run parallel to each other. Instead, the adhesive strips 208, 210 extend along respective directions oriented at 90 degree angles to each other, thereby creating a grid-like configuration when viewed from a direction perpendicular to the backing 202. In this embodiment, the first and second patterns corresponding to first and second series of strips 208, 210, overlap each other at intersection points when the respective patterns are projected onto a common reference plane 214 coplanar with the backing 202.

FIG. 3 highlights four distinct regions 212, 220, 222, 224 that can be identified with respect to either the first or second major surface 204, 206 of the backing 202. These include: (i) a periodic two-dimensional array of gap regions 212 where no coating is present on either side of the backing 202, (ii) first coated regions 220 where only the first strips 208 contact the backing 202, (iii) second coated regions 222 where only the second adhesive strips 210 contact the backing 202, and finally (iv) double-coated regions 224 where both the first and second adhesive strips 208, 210 contact the backing 202 from opposite sides.

The double-coated regions 224 coincide with areas of overlap between the first and second patterns when projected onto the reference plane 214. In some embodiments, the collective area of the double-coated regions 224 is sufficiently small relative to the either the first or second major surface 204, 206, as viewed from a direction perpendicular to the backing 202, to enable clean stretch removal from a bonded substrate in peel mode. Preferably, the overall area of the double-coated regions 224 is less than about 50 percent, less than about 40 percent, less than about 30 percent, less than about 20 percent, or less than about 10 percent of the overall area of the first or second major surface 204, 206 as viewed from a direction perpendicular to the backing 202.

The presence of double-coated regions 224 can be significant during stretch removal because the backing 202 (and associated adhesive) is constrained on both surfaces 204, 206, preventing the adhesive from stretching to reduce the force needed to break the bond to the substrate. Having limited localized regions where stretch removal is constrained allows opposing substrates to be effectively "pinned" to each other in some applications. These pinned regions act to retard adhesive detachment along the double-coated regions 224 and may be desirable in certain applications, though not all.

Still another exemplary embodiment displaying a limited degree of overlap between coated adhesive patterns is shown in FIGS. 5 and 6A-C. These figures show an adhesive article 300 in which the first pattern is a regular array of discrete rectangles defining a first set of adhesive islands 308 contacting and extending across a first major surface 304 of a backing 302. A second pattern, identical to the first pattern but transversely offset along the backing 302, defines a second set of adhesive islands 310 contacting and extending across a second major surface 306 of the backing 302. The first and second patterns corresponding to the adhesive islands 308, 310 slightly overlap each other when the respective patterns are projected onto a common reference plane 314 coplanar with the backing 302. Like article 200, article 300 includes gap regions 312, first and second coated regions 320, 322, and double-coated regions 324.

Figure 7:
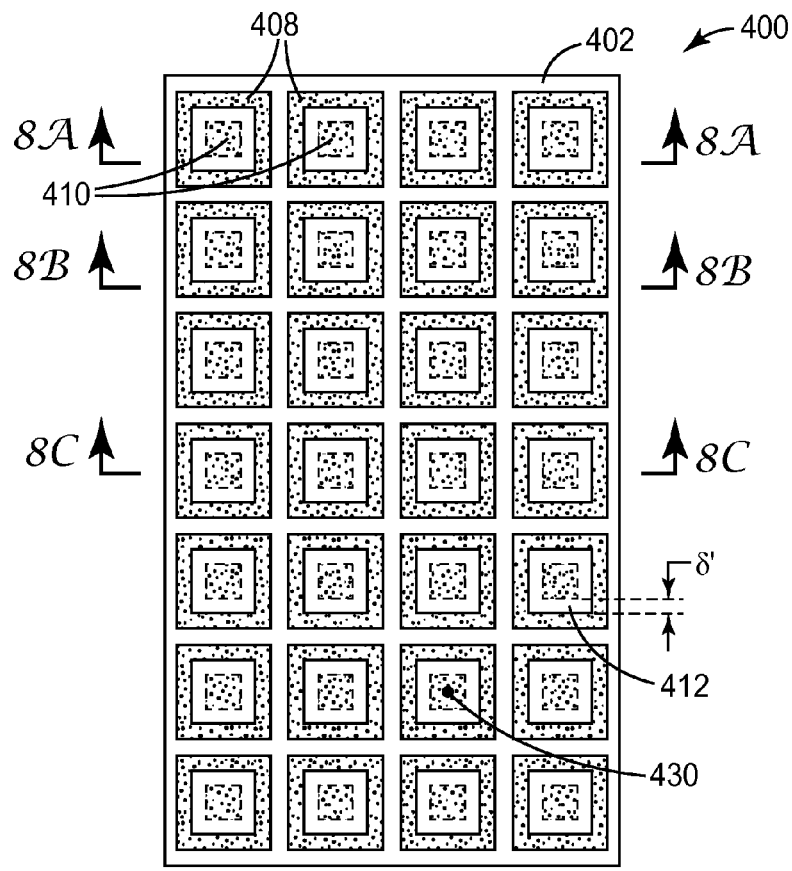
FIG. 7 shows a plan view of a dual-sided adhesive article according to yet another embodiment, looking toward its top surface.
Figure 8A:
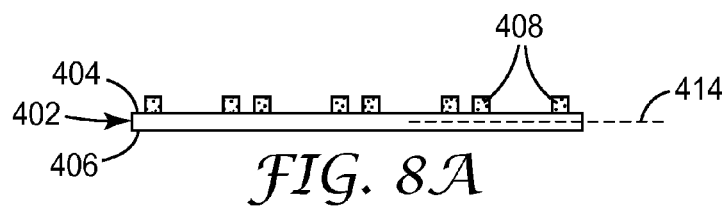
FIGS. 8A-C show three cross-sectional side views of the article of FIG. 7, as defined by consecutive section planes indicated in FIG. 7.
Figure 8B:
Figure 8C:
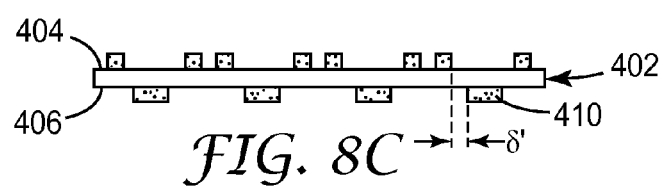

Related embodiments include articles including inverse "checkboard"-type patterns that do not substantially overlap with each other. As another possibility, a gap could be present between checkboard patterns where the corners of the opposing patterns are diagonally spaced apart from each other. Yet another exemplary embodiment is illustrated by FIGS. 7 and 8A-C, which show an adhesive article 400 having a patterned adhesive coating arranged in the form of concentric squares. Referring to FIG. 7, the article 400 has a backing 402 with first and second major surfaces 404, 406 with a first pattern of open adhesive squares 408 on the first major surface 404 and a second pattern of closed adhesive squares 410 on the second major surface 406. As shown, when projected onto a common reference plane 414, the first and second patterns of open and closed adhesive squares 408, 410 do not overlap each other. The first and second patterns are separated by a gap 412 having a fixed, pre-defined gap width δ'. As shown, the gap width δ' is the same along both vertical and horizontal directions. The gap width δ' is largely analogous to the gap width δ defined with respect to the article 100.

The adhesive squares 410 need not be closed. Optionally but not shown here, the adhesive squares 410 of the second pattern are also "open," but sufficiently small in size relative to the adhesive squares 408 to satisfy the condition that there is no substantial overlap between the adhesive squares 408, 410.

Optionally and as shown, one or both adhesive patterns display rotational symmetry to provide similar peeling performance along different directions. Referring again to FIG. 7, for example, the open and closed adhesive squares 408, 410 have a four-fold symmetry about a respective reference axis 430 extending from the geometric center of the squares 408, 410 and perpendicular to the major surfaces 404, 406 of the backing 402. Advantageously, this symmetry can provide identical stretching characteristics along both vertical and horizontal directions. Optionally but not shown, elongated rectangles having an aspect ratio other than 1:1 can also be realized to provide asymmetric stretching characteristics.

Further aspects of the articles 200, 300, 400 are largely analogous to those already discussed with respect to article 100 and need not be repeated.

Adhesive Assemblies

The aforementioned adhesive articles can be manufactured, packaged, and dispensed in a wide assortment of configurations and assemblies depending on the application at hand. For example, the top and bottom of the provided adhesive articles could be coated with liners to protect exposed adhesive surfaces. The liner acts as a release surface and can be integrated into the packaging of the adhesive article or part of an adjoining adhesive article in a stack of adhesive articles, if desired. The adhesive articles could also be continuously manufactured, wound into a roll, and converted for use as a dual-sided tape. This last configuration could further include a dual-sided release liner as in many conventional dual-sided tape constructions.

One or more of the described adhesive articles could come pre-attached to a functional or ornamental article, providing a convenient way to temporarily secure the article to a given surface. As one example, these adhesive articles could be used to secure a poster to a wall, while avoiding damage to the wall when the poster is subsequently removed. As still another configuration, a given adhesive article could be used to join two different substrates, where it is desired at some later time to separate the substrates from each other.

In some embodiments, the assembly includes a permanently bonded substrate having some degree of elasticity. This can advantageously allow the adhesive assembly to be detached and re-positioned on the substrate without distortion. For certain applications, however, it may be beneficial to use a permanently bonded substrate that is relatively inelastic compared with the backing, whereby permanent deformation of the assembly would effectively prevent its re-use.

In an exemplary application, a provided adhesive article attaches an absorbent feminine hygiene pad to an undergarment by means of a suitable pressure-sensitive adhesive ("PSA"). A recurrent problem in this particular application relates to shifting of the pad when the undergarment is worn, as a result of the adhesive not holding well enough. In another failure mode related to a poor adhesive bond, the pad partially or fully detaches from the undergarment. Partial detachment can allow the PSA to fold and stick to itself as a result of movements by the wearer. While these problems can be somewhat alleviated by using a stronger PSA, this often leads to further problems. For example, using a PSA that holds too well can render the pad difficult to remove from the undergarment, damage the undergarment, or leave adhesive residue on the undergarment after removal. All of the above outcomes lead to consumer dissatisfaction.

Figure 9:
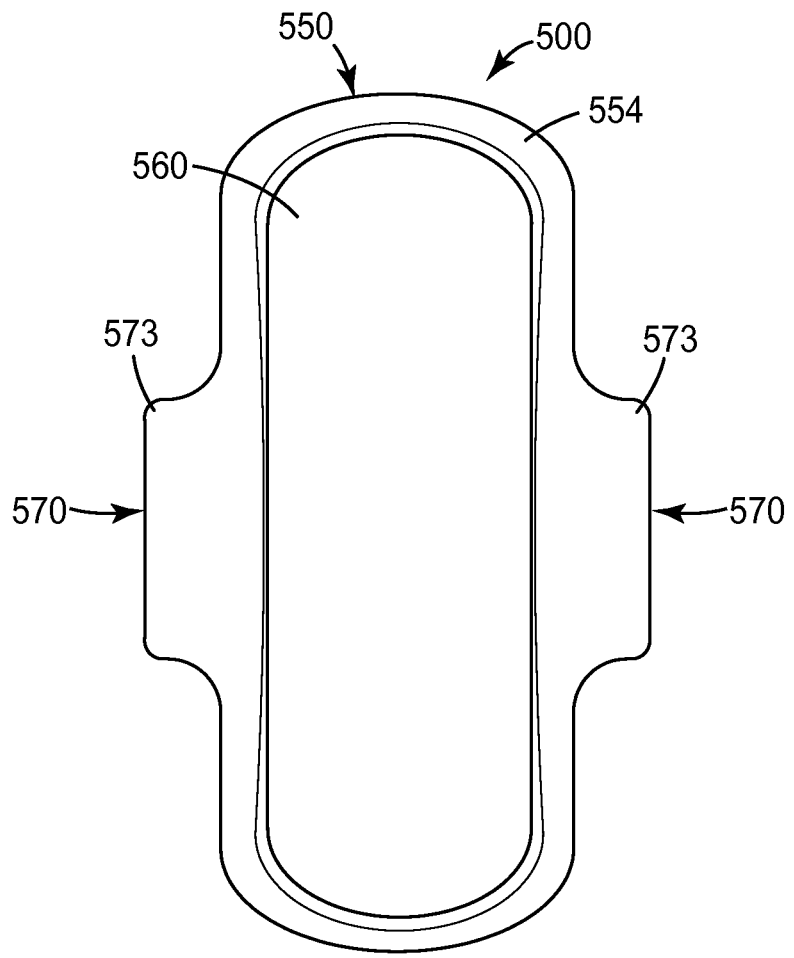
FIG. 9 shows a plan view of a dual-sided adhesive assembly according to another embodiment, looking toward its bottom surface.
Figure 10:
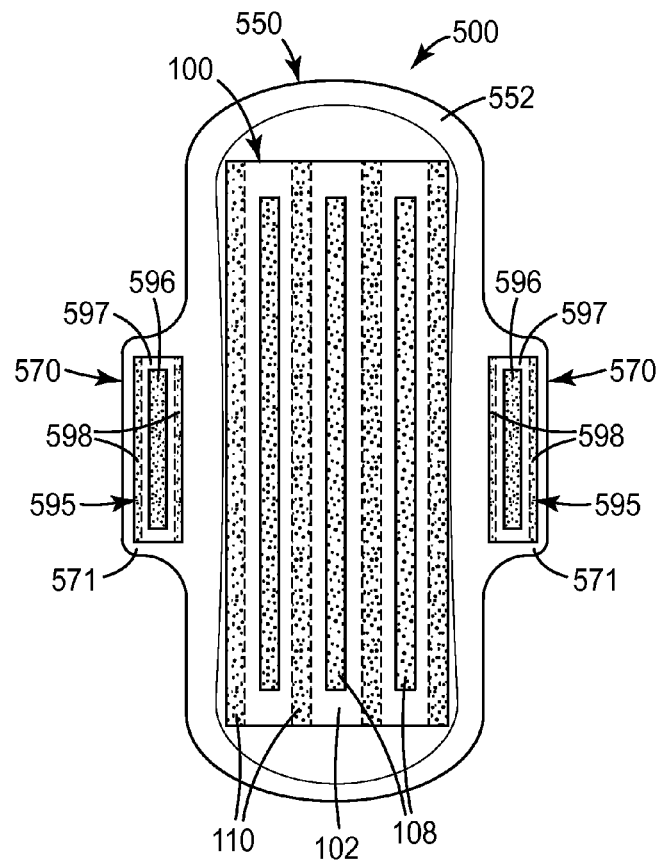
FIG. 10 shows a plan view of the assembly of FIG. 9, looking toward its top surface.

The adhesive articles and assemblies described herein enable a solution to the above dilemma FIGS. 9 and 10 show bottom and top views of an adhesive assembly 500 according to yet another embodiment. The assembly 500 is a feminine hygiene pad having a back layer 550 with top and bottom surfaces 552, 554. In a preferred embodiment, the back layer 550 is flexible and includes a liquid-impermeable or liquid-resistant material. Contacting and extending across the bottom surface 554 of the back layer 550 is an absorbent pad 560. The absorbent pad 560 comes into contact with the body of the wearer during use and functions to collect bodily discharges and prevent soiling of the attached undergarment.

The absorbent pad 560 may include a plurality of layers, such as a permeable topsheet and an absorbent core. Many absorbent core materials are known in the art, including airfelt, cellulose wadding, fibrated communition pulp, tissue paper, and gelling materials such as those provided by Grain Processing Corporation of Muscatine, Iowa. Further options and advantages are described in U.S. Pat. No. 6,200,298 (Osborn et al.).

Referring now to FIG. 10, the adhesive assembly 500 further includes a dual-sided adhesive article for temporarily securing the assembly 500 to an undergarment. In this particular embodiment, the top side 550 is secured to the adhesive article 100 as earlier described and shown in FIG. 1. As illustrated, the four strips 110 adhesively couple the article 100 to the top surface 552 of the back layer 550. The three adhesive strips 108 on the opposite-facing side of the backing 102 are available to adhesively couple the assembly 500 to the wearer's undergarment while in use. The adhesive assembly 500 further includes a pair of wings 570 having top and bottom surfaces 571, 573. The wings 570 can fold over the lateral edges of the undergarment and adhesively couple to its opposing side for improved securement to the undergarment.

Optionally and as shown, an adhesive article 595 is disposed on the bottom surface 571 of each wing 570. The adhesive article 595 is essentially a miniature version of the adhesive article 100 having analogous components, options and advantages. Like the adhesive article 100, each adhesive article 595 includes an elastic backing 597 and adhesive strips 596, 598, and can securely adhering the wing 570 to an undergarment surface while subsequently providing clean and easy stretch removal in a peel mode. Surprisingly, this result was obtained irrespective of the directionality of the peel motion relative to the adhesive strips 596, 598.

Figure 10A:
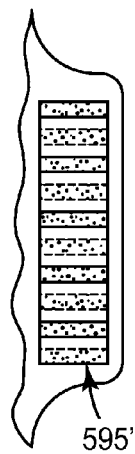
FIGS. 10A-C show fragmentary plan views for three variants of the assembly shown in FIGS. 9-10, with focus on a particular element of the assembly and looking toward its top surface.
Figure 10B:
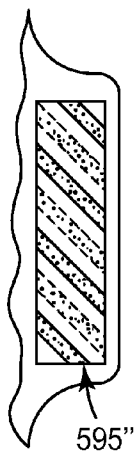
Figure 10C:
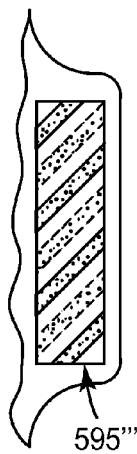

As mentioned previously, the tactile sensation in peeling the assembly 500 from an undergarment can be adjusted based on the adhesive coating pattern. FIGS. 10A-C show alternative embodiments of the article 595 on the wings 570 of the assembly 500. As shown by articles 595', 595", and 595'" in these figures, the adhesive strips of these articles can be oriented along different directions (here, 90°, +45°, and −45° relative to the strip direction in article 595) in the plane of the backing. While not shown here, the adhesive strips may also have a non-uniform width and/or non-uniform spacing.

In other embodiments, the assembly 500 is packaged with a release liner (not shown) that covers the adhesive strips 108, 596 and prevents contamination of exposed adhesive surfaces. This release liner can be easily peeled away from the assembly 500 and discarded prior to use.

The disclosed adhesive articles and assemblies provide numerous advantages over conventional adhesive attachment means for securing feminine hygiene articles to undergarments and stretch removable tapes. First, these configurations enable use of PSAs that achieve high bond strength to the substrate, while allowing these PSAs to detach cleanly and easily from delicate substrates that would otherwise be damaged or destroyed by conventional adhesive constructions. Second, the provided configurations show surprising resistance to adhesive failure, even when bonded to garments subjected to severe twisting and shearing movements—these types of movements have been observed to cause spontaneous detachment of conventional adhesives. Third, the provided configurations preserve the above advantages even when removing in peel mode, which is more intuitive to consumers than stretching the adhesive along a direction parallel to the substrate. Fourth, adhesive coating weight can be substantially reduced in the provided configurations compared with conventional adhesives, resulting in reduced manufacturing costs.

Methods of Use

Figure 11:
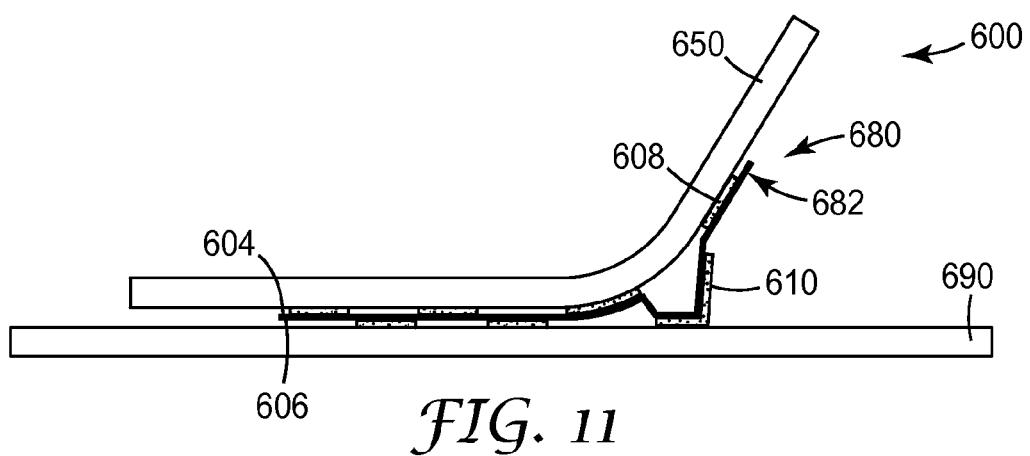
FIG. 11 shows an elevational side view of the assembly of FIGS. 9-10, looking toward its side surface while it is removed from its underlying substrate.

An exemplary mode of detaching a dual-sided adhesive assembly 600 from a substrate 690 is shown in FIG. 11. The assembly 600 includes a flat dual-sided adhesive article 680 affixed to a permanently bonded substrate 650. Like the article 100, the article 680 includes a planar elastic backing 682 with top and bottom surfaces 604, 606, a first adhesive 608 extending across the top surface 604 according to a two-dimensional first pattern and a second adhesive 610 extending across the bottom surface 606 according to a two-dimensional second pattern. In the embodiment shown, there is no overlap between the first and second patterns when viewed from above.

When it is desired to detach the assembly 600 from the substrate 690, a user grasps the substrate 650 and pulls it upwards in a direction away from the substrate 690. As a result of this peeling motion, the first adhesive 608 remains bonded to both the substrate 650 and the backing 682, while both the backing 682 and second adhesive 610 collectively stretch (as shown here, along a direction generally parallel to the backing 682). This stretching takes place along an area of the article 680 that is devoid of the first adhesive 608 and causes the second adhesive 610 to remove cleanly from the substrate 690. Advantageously, the detachment operates in peel mode and therefore does not require stretching of the backing 682 parallel to the plane of the substrate 690 as with conventional stretch removable products.

As a further advantage, a wide range of peel angles can be used to detach the assembly 600 from the substrate 690. For example, the backing 682 can be stretched by pulling the backing 682 away from the substrate 690 at a peel angle of at least 90 degrees, at least 120 degrees, or even at least 135 degrees relative to the substrate 690.

In some embodiments, some degree of stretching of the backing 682 and the first adhesive 608 occurs along a direction generally parallel to the backing 682 along an area of the article 680 that is devoid of the second adhesive 610. Preferably the substrate 690 and the backing 682 stretch collectively and remain adhered to each other, thereby preserving the integrity of the assembly 600.

Although not shown here, the backing 682 could include a non-adhesive pull tab at one end that functions as a handle to peel the backing 682 from the substrate 690 directly. This has the benefit of further reducing risk of unintended detachment between the first adhesive 608 and the backing 682.

Detachment of the adhesive articles can also be actuated along different directions and provide different results. For example, the permanently bonded substrate 650 can be peeled away from the substrate 690 along a direction oriented 90 degrees from the peel direction described above. This peel mode would be achieved, for example, by removing the assembly 500 from a substrate in a direction parallel to the longitudinal axis of the strips 108, 110. Empirically, this was observed to provide similar advantages to the mode of detachment shown in FIG. 11, with an added advantage being a smoother peel (i.e. fluctuations in peel force were greatly attenuated as a function of peel distance). This could provide a significant advantage in user experience, particularly in consumer applications.

In further aspects, methods of detaching adhesive articles are recognized, with exemplary embodiments A-D herein described:

A. A method of detaching from a substrate a generally flat adhesive article having a substantially elastic backing, a first adhesive extending across the top surface according to a two-dimensional first pattern, a second adhesive extending across the bottom surface according to a two-dimensional second pattern, wherein the first and second patterns generally do not overlap each other when viewed from above, the method comprising:
stretching the backing and first adhesive along a direction generally parallel to the backing along an area of the adhesive article that is devoid of the second adhesive to remove the first adhesive from the substrate; and
stretching the backing and second adhesive along a direction generally parallel to the backing along an area of the adhesive article that is devoid of the first adhesive, wherein both the first and second adhesives remain bonded to the backing.

B. The method of embodiment A, wherein stretching the backing comprises peeling the backing at a peel angle of at least 90 degrees relative to the substrate.

C. The method of embodiment B, wherein stretching the backing comprises peeling the backing at a peel angle of at least 120 degrees relative to the substrate.

D. The method of any of embodiments A-C, wherein the substrate is a first substrate and the adhesive article further comprises a second substrate permanently bonded to the backing by the second adhesive.

E. The method of any of embodiments A-D, wherein stretching the backing comprises peeling the second substrate away from the first substrate.

EXAMPLES

Materials

Materials used for the Examples are shown in Table 1.

TABLE 1

Materials List

| Material | Description |
| --- | --- |
| Kraton ™ 1161 | Linear SIS copolymer, Kraton Polymers, Houston, TX |
| Escorez ™ 1310 | Aliphatic hydrocarbon resin, ExxonMobile Chemical, Houston, TX |
| 5550 oil | Heavy hydrotreated naphthenic distillates, Calumet Lubricants Company, Indianapolis, IN |
| Irganox ™ 1076 | CAS 2082-79-3, BASF, Florham Park, NJ |

Test Methods

All testing was conducted at constant temperature (23 deg. C.+/−2 deg. C.) and 50%+/−5% relative humidity. A universal constant rate of extension tensile testing instrument equipped with a computer for data recording and the required load ranges was used (Model 55564 HS available from Instron Engineering Corporation, Canton, Mass.). The instrument crosshead speed was set to 12 inches/min (30.5 cm/min)

A sample of the Example or Comparative adhesive article was applied between a glass plate and a polypropylene film (180 microns thick, 191 grams per square meter (gsm)) with two passes of a 4.5 lb roller. In some cases the adhesive article was applied between the polypropylene film and 20 lb (9.1 kg) white copy paper, or two pieces of 20 lb (9.1 kg) white copy paper.

Peel

The end of the polypropylene film was placed in the upper jaw of the Instron, while the glass plate was placed into the 135 degree stationary jig on the Instron. The instrument was started and the stress-elongation curve was measured. Average load (g(f)) and area under the curve (energy, mJ) were reported. A T-peel measurement (polypropylene laminated to paper) was made for the samples which didn't include the glass plate. Unless otherwise noted, peel was performed in the direction of the strips of adhesive article.

Shear

The end of the polypropylene film was placed in the upper jaw of the Instron instrument, while the glass plate was placed into the 180 degree stationary jig on the Instron. The instrument was started and the stress-elongation curve was measured. Average load (g(f)) and area under the curve (energy, mJ) were reported. The distance the film was pulled until it detached from the glass plate was also measured (cm). Unless noted, shear was performed in the direction of the strips of adhesive article.

EXAMPLES

Adhesive

The adhesive composition is shown in Table 2.

TABLE 2

| Adhesive Composition | |
|---|---|
| Material | % |
| Kraton ™ 1161 | 48.0 |
| Escorez ™ 1310 | 49.5 |
| 55500 oil | 1.5 |
| Irganox ™ 1076 | 1.0 |

The materials in Table 2 were combined in a solvent mixture of 3 parts toluene/1 part heptane (30% solids), knife coated on a release liner, and dried in an oven at 65° C. for 20 minutes. Final coating weight was approximately 35 gsm (grams per square meter).

Elastic Backing

The elastic backing was a B-430 series elastic available from 3M Company (St. Paul, Minn.). This material is a 3-layer laminate consisting of an anisotropic elastic core and a micro-activated, non-elastic polypropylene skin layer surrounding the core.

Example-1 (E-1)

Strips (0.635 cm wide) of adhesive on release liner were cut and adhered to the first side of the Elastic Backing. The strips were rectangular and parallel to adjacent strips which were about 0.95 cm apart. Strips (0.635 cm wide) of adhesive on release liner were then cut and adhered to the second (opposite) side of the Elastic Backing between the strips on the first side. The strips on the opposite sides of the Elastic Backing did not overlap; there was a gap of approximately 0.16 cm.

E-2 Through E-5

E-2 through E-5 were prepared as in E-1 with the gaps shown in Table 4.

Comparative-1 (C-1)

A control was prepared as describe in Example-1, but the entire first side of the Elastic Backing was covered with the adhesive on release liner. The strips on the second side overlapped with the adhesive coating on the first side.

C-2 Through C-4

C-2 was prepared as in C-1. C-3 and C-4 were prepared as in C1 except the polypropylene was laminated to paper instead of glass.

Results

Shear and adhesion data are shown in Tables 3-5. For these samples, the polypropylene film was pulled in the direction of the parallel strips of adhesive.

Shear

As shown in Table 3, the elastic laminate of E-1 required a pull of 2 cm before delamination, while C-1 delaminated after only a 0.4 cm pull.

TABLE 3

| Shear - Polypropylene Laminated to Glass | | | | |
|---|---|---|---|---|
| Sample | Gap (cm) | Avg Load (gf) | Energy (mJ) | Pull Distance to Delamination (cm) |
| E-1 | 0.16 | 3871 | 978 | 2.0 |
| E-2[a] | 0.16 | 4102 | 963 | 2.2 |
| CONTROL (one side of elastic is full adhesive coat) | | | | |
| C-1 | No gap | 2266 | 101 | 0.4 |

[a]adhesive backing strips were 90° of shear direction

Adhesion

Table 4 shows the peel performance of E-2 to E-5, which had a nominal gap width ranging from −0.16 to 0.64 cm, compared with C-2, which had a zero gap width. This data shows that the ability of the backing to stretch during the peel action reduced the adhesion forces, facilitating peel removal.

TABLE 4

| Polypropylene Laminated to Glass Adhesion | | | |
|---|---|---|---|
| Sample | Gap (cm) | Avg Load (gf) [a] | Energy (mJ) [a] |
| E-2 | −0.16 | 405 | 566 |
| E-3 | 0 | 404 | 576 |
| E-4 | 0.16 | 544 | 795 |
| E-5 | 0.64 | 491 | 739 |
| CONTROL (one side of elastic is full adhesive coat) | | | |
| C-2 | No gap | 647 | 942 |

[a] All values are an average of 2 sample measurements.

As shown in Table 5, an elastic backing with strips of adhesive allow cleanly releases from a sensitive material (paper), while an elastic backing which was fully coated on one side tore the paper during removal.

TABLE 5

| Polypropylene Laminated to Paper T-Peel | | | | |
|---|---|---|---|---|
| Sample | Gap (cm) | Avg peel force (gf) | Energy (mJ) | Comments |
| E-6 | 0.16 | 117 | 132 | Clean peel, no delamination |
| E-7 | 0.64 | 141 | 199 | Clean peel, no delamination |
| CONTROL (one side of elastic is full adhesive coat) | | | | |
| C-3 | No gap | 204 | 274 | Paper delaminated |
| C-4 | No gap | 200 | 316 | Paper delaminated |

All of the patents and patent applications mentioned above are hereby expressly incorporated into the present disclosure. The foregoing invention has been described in some detail by way of illustration and example for purposes of clarity and understanding. However, various alternatives, modifications, and equivalents may be used and the above description should not be taken as limiting in the scope of the invention, which is defined by the following claims and their equivalents.

What is claimed is:
1. A dual-sided adhesive article comprising:
 a flat and substantially elastic backing having first and second major surfaces;
 a first adhesive coating the first major surface according to a two-dimensional first pattern; and
 a second adhesive coating the second major surface according to a two-dimensional second pattern, wherein the first and second patterns do not substantially overlap with each other when the first and second patterns are projected onto a reference plane parallel to the backing, whereby areas of the backing coated by the first adhesive on the first major surface are substantially uncoated by the second adhesive on its opposing second major surface and areas of the backing coated by the second adhesive on the second major surface are substantially uncoated by the first adhesive on its opposing first major surface.

2. The article of claim 1, wherein the respective projections of the first and second patterns are generally spaced apart from each other by a gap.

3. The article of claim 2, wherein the first and second patterns are characterized by respective repeat units having a certain repeat dimension and the gap has an average width ranging from 10 percent to 500 percent of the repeat dimension for either the first or second pattern.

4. The article of claim 3, wherein the average gap has a width ranging from 50 percent to 250 percent of the repeat dimension for either the first or second pattern.

5. The article of claim 1, wherein the first and second patterns are discontinuous patterns.

6. The article of claim 5, wherein the first and second patterns comprise first and second sets of discrete parallel strips.

7. The article of claim 6, wherein the first and second sets of strips have respective terminal edges, the terminal edge of the first set being spaced further from the terminal edge of the backing than the terminal edge of the second set.

8. The article of claim 1, wherein the respective projections of the first and second patterns collectively extend across about 10 percent to about 95 percent of the overall surface area of the backing.

9. The article of claim 8, wherein the respective projections of the first and second patterns collectively extend across about 25 percent to about 60 percent of the overall surface area of the backing.

10. The article of claim 1, wherein the first adhesive extends across a first coating area ranging from about 30 percent to about 90 percent of the first major surface.

11. The article of claim 10, wherein the first coating area ranges from about 60 percent to about 75 percent of the first major surface.

12. The article of claim 10, wherein the second adhesive extends across a second coating area ranging from about 30 percent to about 90 percent of the first coating area.

13. The article of claim 12, wherein the second coating area ranges from about 50 percent to about 80 percent of the first coating area.

14. The article of claim 1, wherein either the first or second pattern is a randomized pattern.

15. The article of claim 1, wherein the first or second adhesive has a coating weight ranging from about 5 gsm to about 100 gsm.

16. The article of claim 15, wherein the coating weight ranges from about 20 gsm to about 75 gsm.

17. The article of claim 1, wherein the backing has an elastic recovery of at least 70 percent based on an elongation of 100 percent.

18. The article of claim 17, wherein the backing has an elastic recovery of at least 80 percent based on an elongation of 100 percent.

19. The article of claim 18, wherein the backing has an elastic recovery of at least 90 percent based on an elongation of 100 percent.

20. A dual-sided adhesive article comprising:
a planar backing having first and second major surfaces, the backing displaying elastomeric properties at room temperature;
a first adhesive coating the first major surface according to a two-dimensional first pattern; and
a second adhesive coating the second major surface according to a two-dimensional second pattern, wherein the collective area of overlap between the first and second patterns is less than 20 percent of the overall area of the first or second major surface as viewed from a direction perpendicular to the backing, whereby areas of the backing coated by the first adhesive on the first major surface are substantially uncoated by the second adhesive on its opposing second major surface and areas of the backing coated by the second adhesive on the second major surface are substantially uncoated by the first adhesive on its opposing first major surface.

21. The dual-sided adhesive article of claim 20, wherein the first and second patterns, when projected onto a reference plane parallel to the backing, are generally spaced apart from each other by a gap.

22. An adhesive assembly comprising:
a substrate; and
a dual-sided adhesive article contacting the substrate, the dual-sided article comprising:
a flat and substantially elastic backing having first and second major surfaces;
a first adhesive coating the first major surface along a two-dimensional first pattern;
a second adhesive coating the second major surface and adhering the backing to the substrate according to a two-dimensional second pattern, wherein the first and second patterns do not substantially overlap with each other when the first and second patterns are projected onto a reference plane parallel to the backing, whereby areas of the backing coated by the first adhesive on the first major surface are substantially uncoated by the second adhesive on its opposing second major surface and areas of the backing coated by the second adhesive on the second major surface are substantially uncoated by the first adhesive on its opposing first major surface.

23. The assembly of claim 22, wherein the substrate comprises an absorbent pad.

24. The assembly of claim 22, further comprising a release liner contacting the second adhesive and extending across the second major surface.

25. The assembly of claim 24, wherein the release liner is integrated into a packaging of the assembly.

26. The assembly of claim 22, wherein the backing further comprises a non-adhesive pull tab to facilitate peel removal of the assembly from a bonded substrate.

* * * * *

UNITED STATES PATENT AND TRADEMARK OFFICE
CERTIFICATE OF CORRECTION

Page 1 of 1

PATENT NO. : 8,889,240 B2
APPLICATION NO. : 13/730125
DATED : November 18, 2014
INVENTOR(S) : Leigh Wood It is certified that error appears in the above-identified patent and that said Letters Patent is hereby corrected as shown below:

In the Specification

Column 6
Line 19, delete "6," and insert -- δ, --, therefor.

Column 11
Line 43, delete "dilemma" and insert -- dilemma. --, therefor.

Column 14
Line 39, delete "min)" and insert -- min). --, therefor.

Signed and Sealed this
Nineteenth Day of May, 2015

Michelle K. Lee
*Director of the United States Patent and Trademark Office*